US010888631B2

(12) United States Patent
Kvale et al.

(10) Patent No.: US 10,888,631 B2
(45) Date of Patent: Jan. 12, 2021

(54) LIPID STERILIZATION METHOD

(71) Applicant: GE Healthcare AS, Oslo (NO)

(72) Inventors: Svein Kvale, Oslo (NO); Ingrid Henriksen, Oslo (NO); Ole Johannes Tokerud, Oslo (NO); Per Sontum, Oslo (NO)

(73) Assignee: GE HEALTHCARE AS, Oslo (NO)

( * ) Notice: Subject to any disclaimer, the term of this patent is extended or adjusted under 35 U.S.C. 154(b) by 35 days.

(21) Appl. No.: 15/314,353

(22) PCT Filed: Jun. 26, 2015

(86) PCT No.: PCT/EP2015/064568
§ 371 (c)(1),
(2) Date: Nov. 28, 2016

(87) PCT Pub. No.: WO2015/197836
PCT Pub. Date: Dec. 30, 2015

(65) Prior Publication Data
US 2017/0258950 A1    Sep. 14, 2017

(30) Foreign Application Priority Data

Jun. 26, 2014  (GB) .................................. 1411423.5

(51) Int. Cl.
| | | |
|---|---|---|
| *A61L 2/07* | (2006.01) | |
| *A61K 49/22* | (2006.01) | |
| *A61K 47/24* | (2006.01) | |
| *A61K 9/127* | (2006.01) | |
| *A61K 9/107* | (2006.01) | |
| *A61B 8/08* | (2006.01) | |

(52) U.S. Cl.
CPC .............. *A61L 2/07* (2013.01); *A61K 9/1075* (2013.01); *A61K 9/1277* (2013.01); *A61K 47/24* (2013.01); *A61K 49/22* (2013.01); *A61K 49/223* (2013.01); *A61B 8/481* (2013.01)

(58) Field of Classification Search
CPC ......... A61L 2/07; A61K 49/223; A61K 49/22; A61K 47/24; A61K 9/1075; A61K 9/1277; A61B 8/481
See application file for complete search history.

(56) References Cited

U.S. PATENT DOCUMENTS

| 5,088,499 | A | 2/1992 | Unger |
| 6,217,850 | B1 | 4/2001 | Dugstad et al. |
| 8,415,329 | B1 | 4/2013 | Mishra |
| 2003/0049158 | A1 | 3/2003 | Hui et al. |
| 2008/0057022 | A1* | 3/2008 | Xia .................... A61K 9/0048 424/78.04 |

FOREIGN PATENT DOCUMENTS

| CN | 1518479 A | 8/2004 |
| CN | 1518479 A | 8/2008 |
| CN | 101427784 A | 5/2009 |
| CN | 101636146 A | 1/2010 |
| JP | 03123475 | 5/1991 |
| JP | 2001515055 A | 9/2001 |
| JP | 2004532068 A | 10/2004 |
| JP | 2007314559 A | 12/2007 |
| JP | 4250747 B2 | 4/2009 |
| JP | 2010502634 A | 1/2010 |
| WO | 99/08716 A2 | 2/1999 |
| WO | 9908715 A1 | 2/1999 |
| WO | 9908716 | 2/1999 |
| WO | 9908716 A2 | 2/1999 |
| WO | 99/36104 A3 | 7/1999 |
| WO | 02/082462 A2 | 10/2002 |
| WO | 02082462 A2 | 10/2002 |

OTHER PUBLICATIONS

Kastango, Sterilization and Quality Assurance Procedures, Oct. 10, 2013. (Year: 2013).*
Finn Aqua Bio Pharma Series (BPS) GMP Steam Sterilisers Technical Data Sheet. Jan. 4, 2009 p. 2, section: "Cycle B"; p. 3, section: "steam-air-mix SAMX cycle", "Pressure vessel" Citation is not enclosed due to copyright restrictions. A copy may be obtained from the URL at http://www.sterislifesciences.com/Products/Equipment/Steam-Sterilizers/Finn-Aqua-BPS.
Search Report and Written Opinion from Singapore Patent Application No. 11201610689V, dated Dec. 18, 2017, 8 pages.
Written Opinion in correspondence to Singapore Application No. 11201610689V, dated Oct. 4, 2018.
"Finn-Aqua Bio Phrama Series (BPS) GMP Steam Sterilizers", Steries Life Sciences Group, published 2012.
Japan Notice of Preliminary Rejection corresponding to Japanese Application No. 2016-573023, dated Mar. 12, 2019.
Sontum, Per C., "Physicochemical Characteristics of Sonazoid(TM), A New Contrast Agent for Ultrasound Imaging", Ultrasound Med. & Biology, vol. 34, No. 5, pp. 824-833, 2008.
Taiwan Office Action and Examination Report corresponding to Taiwanese Application No. 104120688, dated Aug. 22, 2019 (with English translation).
China Search Report and Office Action corresponding to Chinese Application No. 2015105282225.5, dated May 22, 2019.
"Finn-Aqua Pharmaceutical GMP Steam Sterilizer", Steris, URL: [http://www.equipnet.com/mp_data/media/200971133_180559_1.pdf] Jan. 1, 2004.

(Continued)

*Primary Examiner* — Michael G. Hartley
*Assistant Examiner* — Leah H Schlientz
(74) *Attorney, Agent, or Firm* — Jeff B. Vockrodt; Culhane Meadows, PLLC

(57) ABSTRACT

The present invention relates to a method for sterilisation of phospholipid suspensions, useful in the preparation of ultrasound contrast agent precursors comprising phospholipid-stabilised perfluorobutane microbubbles. The method provides sterility assurance, without undue thermal degradation of the phospholipid. The method is also amenable to commercial scale manufacture. Also provided are methods of preparing kits and ultrasound contrast agents incorporating the sterilisation method of the invention.

10 Claims, 6 Drawing Sheets

(56) References Cited

OTHER PUBLICATIONS

Gaysorn Chansiri et al., "Effect of surface charge on the stability of oil/water emulsions during steam sterilization", Journal of Pharmaceutical Sciences, vol. 88, No. 4, Apr. 1, 1999.
Steris, "Finn-Aqua Pharmaceutical GMP Steam Sterilizer", dated Jan. 5, 2004, 10 pages.
GB Search Report regarding GB Application No. 1411423.5, dated Dec. 22, 2014, 3 pages.
International Search Report and Written Opinion regarding International Application No. PCT/EP2015/064568, dated Nov. 9, 2015, 19 pages.
Tardi et al., "Steam Sterilisation of vesicular phospholipid gels," International Journal of Pharmaceutics, vol. 217, 2001 pp. 161-172.

\* cited by examiner

LIPID STERILIZATION METHOD

CROSS-REFERENCE TO RELATED APPLICATIONS

This application is a filing under 35 U.S.C. 371 of international application number PCT/EP2015/064568, filed Jun. 26, 2015, which claims priority to GB application number 1411423.5, filed Jun. 26, 2014, the entire disclosures of each of which are hereby incorporated by reference.

FIELD OF THE INVENTION

The present invention relates to a method of sterilisation of phospholipid suspensions, useful in the preparation of ultrasound contrast agent precursors comprising phospholipid-stabilised perfluorobutane microbubbles. The method provides sterility assurance, without undue thermal degradation of the phospholipid. The method is also amenable to commercial scale manufacture. Also provided are methods of preparing kits and ultrasound contrast agents incorporating the sterilisation method of the invention.

BACKGROUND TO THE INVENTION

Ultrasound contrast agents based on phospholipid-stabilised microbubbles of perfluorocarbons (e.g. perfluoropropane or perfluorobutane), are well known in the art [see e.g. Wheatley et al, J. Drug Del. Sci. Technol., 23(1), 57-72 (2013)].

WO 97/11683 discloses that phospholipids undergo hydrolysis, and addresses the need for stabilising such compositions during autoclaving (page 6, 1st full paragraph). WO 97/11683 teaches the use of stabilising buffers at a pH of less than or equal to 9.5, to seek to prevent degradation of phospholipids during autoclaving.

WO 97/29782 teaches that ultrasound contrast agent precursors which are stable at room temperature can be prepared by lyophilization of perfluorocarbon microbubbles in the presence of a freeze-drying stabiliser chosen from: sucrose, maltose, trehalose, raffinose or stachyose, preferably sucrose. WO 97/29782 also teaches that the content of phosphatidylserine phospholipids used to stabilise such contrast agents can be reduced during heat sterilisation.

WO 99/08715 discloses a process for the preparation of a pharmaceutical composition comprising an aqueous dispersion of gas-containing vesicles the membranes whereof comprise an amphiphilic membrane-forming material, said process comprising:
 (i) generating a liquid dispersion of gas-containing vesicles from a mixture comprising an amphiphilic membrane forming material;
 (ii) lyophilizing a liquid dispersion of said gas-containing vesicles;
 (iii) reconstituting the lyophilized product of step (ii) with a sterile aqueous liquid to produce an aqueous dispersion of gas-containing vesicles; and
 (iv) treating the aqueous dispersion product of step (i) or step (iii) or the lyophilized product of step (ii) to produce a substantially aggregate-free sterile aqueous dispersion of gas-containing vesicles.

EP 1228770 A1 teaches a process for the preparation of lyophilised ultrasound contrast agents comprising gas microbubbles, in which the vials of lyophilised precursor are sealed under a reduced pressure of the headspace gas. The reduced pressure is said to assist in controlling the particle size in the aqueous microbubble composition formed post-reconstitution of the precursor vial.

Feshitan et al [J. Coll. Interf. Sci., 329, 316-324 (2009)] report that, in contrast to surfactant-coated microbubbles, lipid-coated microbubbles are stable after centrifugation, and that the lipid shell is highly viscous and relatively impermeable to gases. Feshitan et al report that perfluorobutane microbubbles in the 4-5 µm size range were stable for at least 2-days, but tended to disintegrate into smaller size microbubbles (1-2 µm) after 2-weeks.

There is still a need for ultrasound lyophilised precursor preparation methods for agents which incorporate phospholipids, which give control over the sterility of the product. Such methods of phospholipid sterilisation need to be amenable to commercial scale manufacture, and deliver precursor products with a uniformity of vial content and safety profile which satisfy the regulatory requirements (e.g. U.S. Pharmacopeia and ICH Guidelines).

THE PRESENT INVENTION

Phospholipid-stabilised gas microbubble ultrasound contrast agents intended for parenteral mammalian administration need to be prepared in sterile form. Terminal sterilisation is not a suitable technique for such contrast agents, hence phospholipid suspensions in sterile form are needed to permit aseptic manufacture. Commercial scale contrast agent manufacture requires that large volumes (multi-litre) must be sterilised.

The present inventors have found that thermal degradation of the phospholipids in hydrogenated egg phosphatidylserine can occur on autoclave sterilisation. Thus, phospholipids are thermally-sensitive, and can undergo degradation on prolonged heating at elevated temperatures. Furthermore, if too much degradation occurs during attempted sterilisation, the desirable ultrasound characteristics of the gas microbubble can be compromised. There is thus a problem in achieving thorough sterilisation, without undue thermal degradation of the phospholipid.

This problem is exacerbated on a multi-litre scale, since the larger volumes make it more difficult to ensure uniform heat distribution throughout the system—with the risk that any localised overheating or prolonged exposure will lead to higher levels of phospholipid degradation.

During a standard autoclave process, typically performed in a jacketed steel vessel, heat is delivered to the bulk material by passing a heating medium (normally steam) through an external jacket on the outside of the vessel, isolated from the inner part of the sterilisation system. Such a system hence utilises sensible heat to deliver the energy needed to obtain an acceptable sterilisation. However, in this case, sterilisation system extremities such as inlet ports, sterile filters for venting and tank tops receive heat at a later point in time than the bulk of the material, which is closer to the heating source. All parts of the closed system must be sterilised, and this typically leads to very high heat loads (and $F_0$ values) for the bulk of the material before sterilisation barriers at the extremities reach the accepted minimum level.

Hence, with a standard heating regimen the overall heat load and thus chemical degradation of the phospholipid may become unacceptably high. There is therefore a need for quick and homogeneous heating/cooling of the entire sterilisation system (i.e. the volume contained between the sterilization barriers).

The present invention provides a solution to this problem. The method of the invention comprises steam injection into the phospholipid suspension itself and/or the headspace above said suspension. Utilising latent heat (steam heating) for heat transfer is far more effective than sensible heat from e.g. an external jacket, as a much higher amount of energy is released in a shorter period of time. In addition, injection of steam to the headspace specifically allows for rapid heating of extremities such as inlet ports, sterile filters and tank tops and hence reduces the total heat load on the bulk material. Utilising headspace steam heating offers the following advantages:

| Property | Advantage |
|---|---|
| Rapid, even heating through latent heat transfer | Improved heating of system extremities with ensuing lowering of the heat load inflicted on the bulk material, decreased degradation and improved product quality and productivity |
| Pressure control temperature | Target temperature can be quickly and precisely established |
| High heat transfer coefficient | Smaller required heat transfer surface area, enabling reduced initial equipment outlay. |

DETAILED DESCRIPTION OF THE INVENTION

In a first aspect, the present invention provides a method of sterilisation of a phospholipid suspension, which comprises:
(i) mixing said phospholipid together with propyleneglycol in an aqueous biocompatible carrier in a jacketed vessel to give an aqueous phospholipid suspension; and
(ii) autoclaving the aqueous phospholipid suspension from step (i), wherein said autoclaving enables reaching $F_0$ values >15 in all parts of the sterilization system, and wherein heating, in addition to sensible heat from heating the jacket of said vessel, comprises the addition of steam to:
 (a) the headspace of the vessel of step (i); or
 (b) the aqueous phospholipid suspension of step (i); or
 (c) a combination of (a) and (b);
(iii) cooling the hot suspension from step (ii) to 15 to 30° C. to give the sterile phospholipid suspension;
wherein said phospholipid is hydrogenated egg phosphatidylserine (H-EPS).

The term "sterilisation" has its' conventional meaning, and refers to a process of destruction of micro-organisms, to obtain a sterile, pyrogen-free composition. The term "autoclaving" has its' conventional meaning, and refers to one particular method of sterilisation which uses superheated steam to sterilise. Autoclaving and other sterilisation methods are described in *Achieving Sterility in Medical and Pharmaceutical Products*, N. Halls (CRC Press, 1994).

The term "sterilisation system" means the volume contained within the sterilisation barriers (i.e. inlet and outlet) of the bulk autoclaving unit.

Assurance of sterilization is normally described through the term $F_0$, defined as "the equivalent amount of time, in minutes at 121° C., which has been delivered to a product by the sterilization process" (FDA "Proposed rules" of Jun. 1, 1976 (b), section 212.3). During an autoclave cycle the $F_0$ value is calculated as:

$F_0 = \Delta t \Sigma 10^{(T-Tb)/Z}$ where:
$\Delta t$ is the measurement interval,
T is the heating temperature (temperature measured by the sensor),
Tb is 121.1° C. (defined temperature for steam pasteurisation), and
Z is a temperature constant for logarithmic sterilisation capability changes normally set to 10° C.

During an autoclave cycle, $F_0$ will hence rise with time even at low temperatures, but the rate increase is very dependent upon temperature. According to the USP/Ph. Eur., the minimum requirement for $F_0$ accepted as an assurance of sterility is $F_0 > 15$.

The term "headspace" has its' conventional meaning, and refers to the gas phase within the vessel and over the vessel liquid and/or solid contents—in this case the aqueous phospholipid suspension.

The term "aqueous phospholipid suspension" refers to a suspension of the phospholipid in an aqueous solvent, which comprises water and/or water-miscible solvents. The aqueous solvent is suitably a biocompatible carrier. By the term "biocompatible carrier" is meant a fluid, especially a liquid, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection (WFI), isotonic saline or phosphate buffer. Hence the aqueous suspension suitably excludes water-immiscible organic solvents.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

PREFERRED EMBODIMENTS

In the method of the first aspect, the addition of steam is preferably to the headspace of the vessel of step (i). Thus, whilst steam injection directly into the liquid suspension is possible, addition to the headspace confers a much more controlled heating effect—since injection into the liquid could lead to local, pronounced degradation.

The method of the first aspect is preferably carried out such that the $F_0$ values reached are at least 15 and not more than 25. Thus, the present inventors have established that more prolonged autoclave heating times where $F_0$ reaches 30 lead to undue degradation of the phospholipid. That in turn has an adverse effect on the stability of the PFB microbubbles prepared therefrom.

Thermal degradation of phosphatidylserine is believed to occur as shown in Scheme 1:

Scheme 1

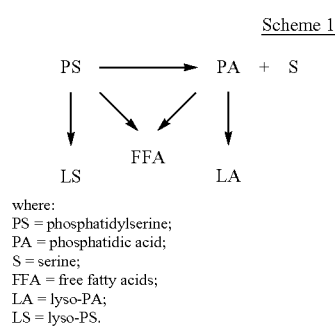

where:
PS = phosphatidylserine;
PA = phosphatidic acid;
S = serine;
FFA = free fatty acids;
LA = lyso-PA;
LS = lyso-PS.

The principal reaction is the hydrolysis of PS to PA and S as shown in Scheme 2:

Scheme 2

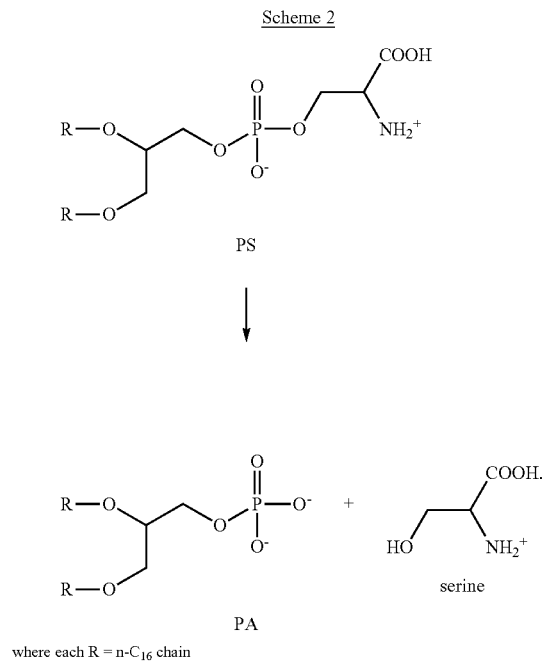

where each R = n-$C_{16}$ chain

Without wishing to be bound by theory, it is believed that increasing degradation means increasing levels of PA, which is an acid. That is more negatively charged than PS (the parent phospholipid), and hence the charge balance and possibly electrostatic repulsive forces of the phospholipid 'shell' stabilising the microbubble are affected.

From Scheme 1 it is clear that the amount of PS in the suspension after autoclaving, relative to the total amount of PS and related substances (i.e. sum of PS, PA, S, FFA, lyso-PA and lyso-PS), is a direct measure of degradation. As is apparent from Example 4, the percentage amount of PS in the total amount of PA and related substances should preferably be at least 68%, more preferably at least 73%, most preferably at least 75%. Lower PS levels have been shown to lead to inferior microbubble characteristics.

In the method of the first aspect, the mass ratio of phospholipid to propyleneglycol is preferably 1:1.5 to 1:2.5, more preferably 1:2.

In the method of the first aspect, the volume of the aqueous phospholipid suspension of step (i) is preferably in the range 20 to 80 L, more preferably 30 to 70 L, most preferably 40 to 60 L.

Sterilisation of phospholipid mixtures, particularly on a multi-litre scale suitable for commercial manufacture is a challenge. That is because the thermal degradation described above competes with the heating necessary to ensure sterilisation. Sterile filtration of the lipid suspension has been proven to reduce the yield and quality of the microbubbles produced in the subsequent manufacturing step and gamma irradiation is not a suitable in-process sterilization technique. Thus, acceptable sterility assurance is difficult to achieve; since larger volumes require longer heating times to obtain the required sterility assurance of $F_0>15$.

To achieve this, the present invention uses steam supplied directly to the vessel headspace. In the method of the first aspect, clean steam (as defined in GMP guidelines CFR Title 21, Part 211) is preferably used in step (ii). The method of the first aspect preferably further comprises the application of a vacuum pulse or multiple vacuum pulses to the headspace of the vessel of step (i), to remove the headspace gas, before the addition of steam to said headspace. The headspace gas is mostly air, which is a good insulator, and removing this before steam injection greatly improves the ensuing heat transfer.

In the method of the first aspect, the vessel of step (i) is suitably a jacketed vessel (as shown for example in FIG. 1), such that the heating of step (ii) further comprises the addition of heated steam to the vessel jacket—i.e. the heating method of the present invention is supplemented by more conventional heating methods to maximise the heat transfer. Through the medium inlet port (FIG. 1, Point A), vacuum is then drawn in cycles from the headspace of the vessel. With the first vacuum pulse, most of the air in the headspace is withdrawn, followed by a pressure build up again due to vaporisation of the liquid in the tank. A new vacuum cycle is applied to withdraw the mixture of remaining air and water vapour. Most preferably, three vacuum pulses are applied before injection of steam. These pulses remove all the air in the vessel headspace and system extremities such as the air filter (FIG. 1, Point B) and the medium inlet.

Injection of clean steam is preferably performed multiple times during the cycle, for example at the start and at the end of the autoclave cycle. The first injection helps to heat the vessel top (FIG. 1, Point C), normally a high heat capacity steel structure, which, if not heated with steam, will cause the autoclave cycle to be prolonged significantly with ensuing excessive degradation of the bulk lipid suspension, as shown in Example 1.

Typically three temperature sensors are included in the sterilizing system; one in the bulk lipid suspension (FIG. 1, Point D), one just outside of the sterile barrier (valve) of the medium inlet (FIG. 1, Point E) and one just outside the sterile barrier of the sterile venting filter (FIG. 1, Point F). For an acceptable sterilization cycle the requirement is $F_0>15$ for all sensors.

A later clean steam injection is preferably performed when the liquid phase reaches $F_0>15$ (normally a set point of $F_0$ of >16 is applied to allow for uncertainty). This injection quickly sterilises the surfaces of vessel top, the air filter and the medium inlet and prevents a prolonged exposure to the sensible heat from the vessel jacket and further degradation of the lipids in the bulk material, as shown in Example 2. When $F_0>16$ is reached in the air filter and media inlet the product is quickly cooled down by applying cooling water to the vessel jacket.

Condensate from the clean steam that is added during the first part of the autoclave cycle also compensates for some of the water evaporating from the H-EPS suspension during the autoclave cycle.

H-EPS is commercially available from NOF Corporation, Amagasaki-Shi, Hyogo, Japan. Techniques for the analysis and quantification of the phospholipid components of egg phosphatidylserine and the ultrasound contrast agent Sonazoid™ have been described by Hvattum et al [J. Pharm. Biomed. Anal., 42, 506-512 (2006)]. Such analyses are also suitable for use in the methods of the present invention.

In a second aspect, the present invention provides a method of preparation of an ultrasound contrast agent precursor which comprises a lyophilised composition of microbubbles of perfluorobutane stabilised by hydrogenated egg phosphatidylserine in sucrose; wherein said method comprises:

(i) carrying out the method of the first aspect, to obtain a sterile aqueous suspension of hydrogenated egg phosphatidylserine;
(ii) forming microbubbles of perfluorobutane in the suspension from step (i) to give an aqueous suspension of perfluorobutane microbubbles stabilised by hydrogenated egg phosphatidylserine;
(iii) diluting the suspension from step (ii) with a sterile sucrose aqueous solution to give a final sucrose concentration of 5-20% w/v;
(iv) dispensing an aliquot of the composition from step (iii) into a vial to give a filled vial;
(v) freeze-drying the filled vials from step (iv);
(vi) back-filling the headspace gas in the freeze-dried vials from step (v) with perfluorobutane;
(vii) sealing each of the vials from step (vi) with a closure.

Preferred embodiments of the method of step (i) in the second aspect are as also described in the first aspect (above).

The term "precursor" refers to a convenient or kit form of the contrast agent, designed so that, upon reconstitution, it readily forms the desired ultrasound contrast agent.

The term "contrast agent" has its' conventional meaning in the field of in vivo medical imaging, and refers to an agent in a form suitable for mammalian administration, which assists in providing clearer images in the region or organ of interest than could be obtained by imaging the mammalian subject alone. By the term "subject" is meant a mammal in vivo, preferably the intact mammalian body in vivo, and more preferably a living human subject. By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

As with other in vivo imaging agents, the contrast agent is designed to have minimal pharmacological effect on the mammalian subject to be imaged. Preferably, the contrast agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

The term "microbubble" has its' conventional meaning in the field of in vivo ultrasound imaging, and refers to a gas microbubble of diameter typically between 0.5 and 10 μm. At sizes above 7 μm there is a substantial risk of retention (embolization) in the lung capillaries. Suitable microbubbles are similar in size to a red blood cell, which allow them to display similar characteristics in the microvessels and capillaries throughout the mammalian body [Sirsi et al, Bubble Sci. Eng. Technol., 1(1-2), 3-17 (2009)].

Suitable microbubbles of the present invention are stabilised by the phospholipids present in hydrogenated egg phosphatidylserine (H-EPS). The phospholipids present in H-EPS are primarily phosphatidylserine and phosphatidic acid [Hvattum et al, J. Pharm. Biomed. Anal., 42, 506-512 (2006)].

Perfluorobutane ("PFB") has its' standard chemical meaning, and is also referred to in the context of medical uses as perflubutane. The chemical formula of perfluoro-n-butane is $CF_3CF_2CF_2CF_3$ or $C_4F_{10}$, with a boiling point of −2.2° C. Commercial perfluoro-n-butane contains a minor amount (typically 2-4%) of the perfluoro-iso-butane isomer, i.e. $CF_3CF(CF_3)CF_3$.

In the method of the second aspect, the sucrose concentration of step (iii) is preferably 8-12% w/v, more preferably about 10% w/v, most preferably 92 mg/mL. The sucrose acts as a lyoprotectant/cryoprotectant, and has been shown to form a matrix wherein the lipid-stabilised PFB microbubbles are trapped within the lyophilised sucrose of the precursor, such that the microbubble size and concentration are predefined—and not influenced by the reconstitution procedure adopted by the end user. Thus, upon reconstitution of the precursor vial with a suitable aqueous medium, the sucrose dissolves releasing the phospholipid-stabilised PFB microbubbles [Sontum, Ultraso. Med. Biol., 34(5), 824-833 (2008)]. The use of sugars as lyoprotectants or cryoprotectants is well known in the art, and is described in e.g. Solis et al [Int. J. Pharmaceut., 396, 30-38 (2010)] and references therein.

The term "filled vial" refers to a charged vial, a vial into which has been dispensed an aliquot of the composition, i.e. a dispensed vial. The vial is not physically full, since the vial volume will typically be 10 mL, and the dispensed volume about 2 mL—leaving a headspace gas above the composition. The term 'headspace gas' has its' conventional meaning, and refers to the gas within the vial over the lyophilised composition.

In the method of the second aspect, the lyophilized precursor composition is sterile.

In the method of the second aspect, the batch size is preferably in the range 500 to 80,000 more preferably 1,000 to 50,000 most preferably 5,000 to 45,000 vials to be filled with contrast agent precursor. A batch size of about 35,000 to 40,000 vials is ideal.

The microbubble preparation of step (ii) of the method of the second aspect can be carried out by a variety of methods known in the art, including:

(i) sonication;
(ii) high shear emulsification;
(iii) membrane emulsification;
(iv) coaxial electrohydrodynamic atomisation (CEHDA); and
(v) microfluidic devices;
(vi) ink jet printing.

These methods are described by Stride et al [Soft Matter, 4, 2350-2359 (2008)] and references therein. Further details of microbubble preparation methods are provided by Unnikrishnan et al [Am. J. Roentgenol., 199(2), 292-299 (2012)].

Ink-jet printing is reported by Stride et al (above) to be more suited to liquid-filled particles, so is less suitable for the PFB microbubbles of the present invention. Sonication is less preferred, since it tends to give a wide range of bubble sizes, and microfluidic techniques suffer from problems with slow production rates unsuitable for commercial manufacture [Wang et al, Ultraso. Med. Biol., 39(5), 882-892 (2013)].

A preferred production method of the present invention is high shear emulsification, preferably using a rotor stator mixer—since that confers a greater degree of size control, is amenable to large batch production, and provides a static size distribution. The microbubbles are formed by agitating a sterile, pyrogen-free lipid suspension in the presence of the perfluorocarbon (here PFB) for several seconds. Example 3 provides a rotor stator microbubble preparation method. Rotor-stator mixers are described in Rodgers et al [Chem. Eng. Res. Rev., 90(3), 323-327 (2012) and in *Emulsion Formation and Stability* [T. F. Tadros (Ed), Wiley VCH (2013)]—see especially Pacek et al Chapter 5 *Emulsification in Rotor-Stator Mixers*, p. 127-167.

The method of the present invention is especially suitable for use in commercial scale production, e.g. of numbers of vials of contrast agent precursor up to 100,000 in a production batch, typically around 35,000 to 40,000. In such large scale, commercial manufacture, consistency from vial-to-vial, i.e. minimising vial-to-vial variation is important. Such batch sizes necessitate the multi-litre volumes of phospholipid suspension as described in the first aspect (above).

A preferred ultrasound contrast agent and precursor of the invention is Sonazoid™ (GE Healthcare AS), previously known as NC100100, as described by Sontum [Ultraso. Med. Biol., 34(5), 824-833 (2008)].

Suitable vials and closures for use in the method of the first aspect are pharmaceutical grade, and suitable for lyophilisation, and are widely available commercially. It is preferred to use a flat-bottomed vial, since that increases the heat transfer between the vial and the shelf of the freeze-drier. The closures are preferably chosen to be suitable for lyophilisation, and designed to permit escape of the vapour out of the vials—making it possible to stopper the vials before the freeze-drier is opened and unloaded.

Sucrose is also commercially available—pharmaceutical grade should be used. Perfluorobutane of pharmaceutical GMP grade can be obtained from F2 Chemicals Limited.

In a third aspect, the present invention provides a method of preparation of a kit for the preparation of an ultrasound contrast agent which comprises:
  (i) carrying out the method of the second aspect to give a vial containing the contrast agent precursor as defined therein; and
  (ii) provision of a container of sterile, aqueous medium suitable for reconstituting said vial of precursor from step (i) to give said contrast agent;
  wherein said ultrasound contrast agent comprises a suspension of microbubbles of perfluorobutane stabilised by hydrogenated egg phosphatidylserine in said sterile, aqueous medium.

Preferred embodiments of the method of the second aspect, precursor and contrast agent in the kit preparation method of the third aspect, are as described in the first and second aspects (above).

The term "kit" here has its' conventional meaning in the field of in vivo imaging, and refers to the imaging agent itself, or a precursor thereto, supplied with all the necessary components to prepare the contrast agent of interest in a form suitable for mammalian administration (as defined above). Such kits are designed to have a usable shelf-life of several weeks or months, such that the clinician can prepare the imaging agent at a suitable juncture and time for imaging the mammalian subject of interest. This is typically more convenient for the clinician, since once prepared, the contrast agent itself will have a much shorter usable shelf-life. Having a supply of the kits means that the clinician has 24-hour, 7-day access to the contrast agent, whenever it is needed. The kit would suitably include a "package leaflet" defining the kit and its components, providing details of how to use the kit, together with patient safety information, and details of the commercial supplier. Such kits typically represent the preferred format of a commercial product designed to provide the ultrasound contrast agent.

The sterile, aqueous solution of step (ii) of the third aspect is preferably a "biocompatible carrier" as defined above. More preferably, it is sterile water for injection. Most preferably, the sterile, aqueous solution has a total concentration of free (i.e. not chelated) aluminium, barium, magnesium, calcium and zinc ions of less than 100 μM, ideally less than 50 μM.

The kit of the second aspect preferably further comprises a vented filter (5 μm) spike such as a Chemoprotect® spike (Codan GmbH & Co, Germany). The kit is reconstituted with the aqueous solution through the spike, followed by manual mixing for about one minute giving a milky, homogeneous dispersion. The dose of contrast agent for imaging the subject is then drawn into a syringe through the filter spike. The role of the "spike" is to remove any extraneous particles or agglomerates—which would be otherwise difficult to detect by visual inspection, since the dispersion within the vial is opaque.

In a fourth aspect, the present invention provides a method of preparation of an ultrasound contrast agent which comprises:
  (i) carrying out the method of the second aspect, to give a vial containing the contrast agent precursor as defined therein; and
  (ii) reconstituting the vial of precursor from step (i) with a sterile aqueous solution;
  wherein said ultrasound contrast agent comprises a suspension of microbubbles of perfluorobutane stabilised by hydrogenated egg phosphatidylserine in said sterile, aqueous medium.

Preferred embodiments of the method of the second aspect, precursor and contrast agent in the contrast agent preparation method of the fourth aspect, are as described in the first and second aspects (above). The method of the fourth aspect is preferably carried out using the kit as described in the third aspect.

Figure 2:
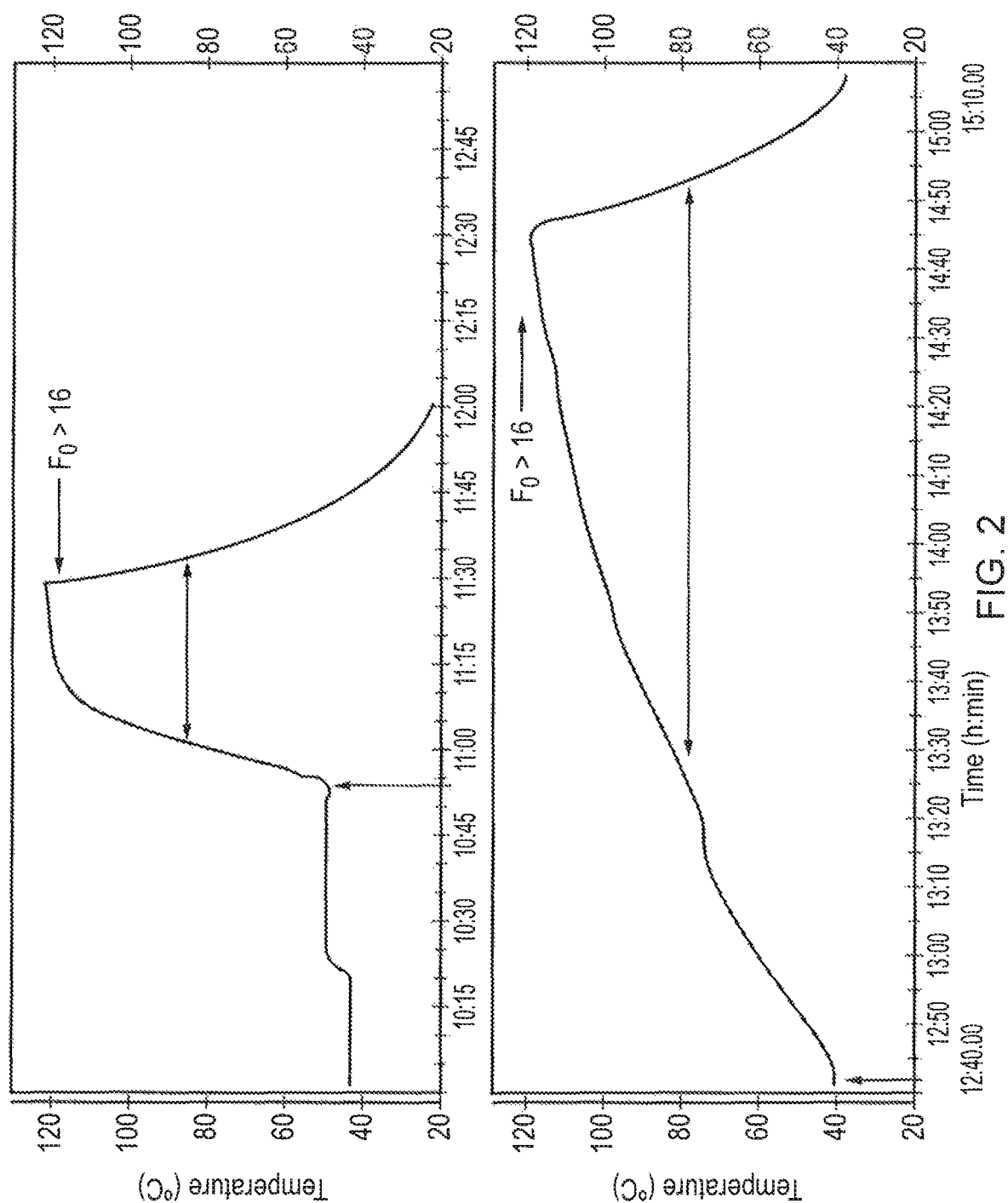
FIG. 2 shows the temperature vs. time from the bulk product sensor for an autoclave cycle using steam injection and heating jacket (upper) and an autoclave cycled using heating jacket only (bottom). Arrows indicate the start of heating/steam injection and time point for $F_0>16$. Double arrows indicate the timespan for bulk product achieving a temperature >80° C.
Figure 3A:
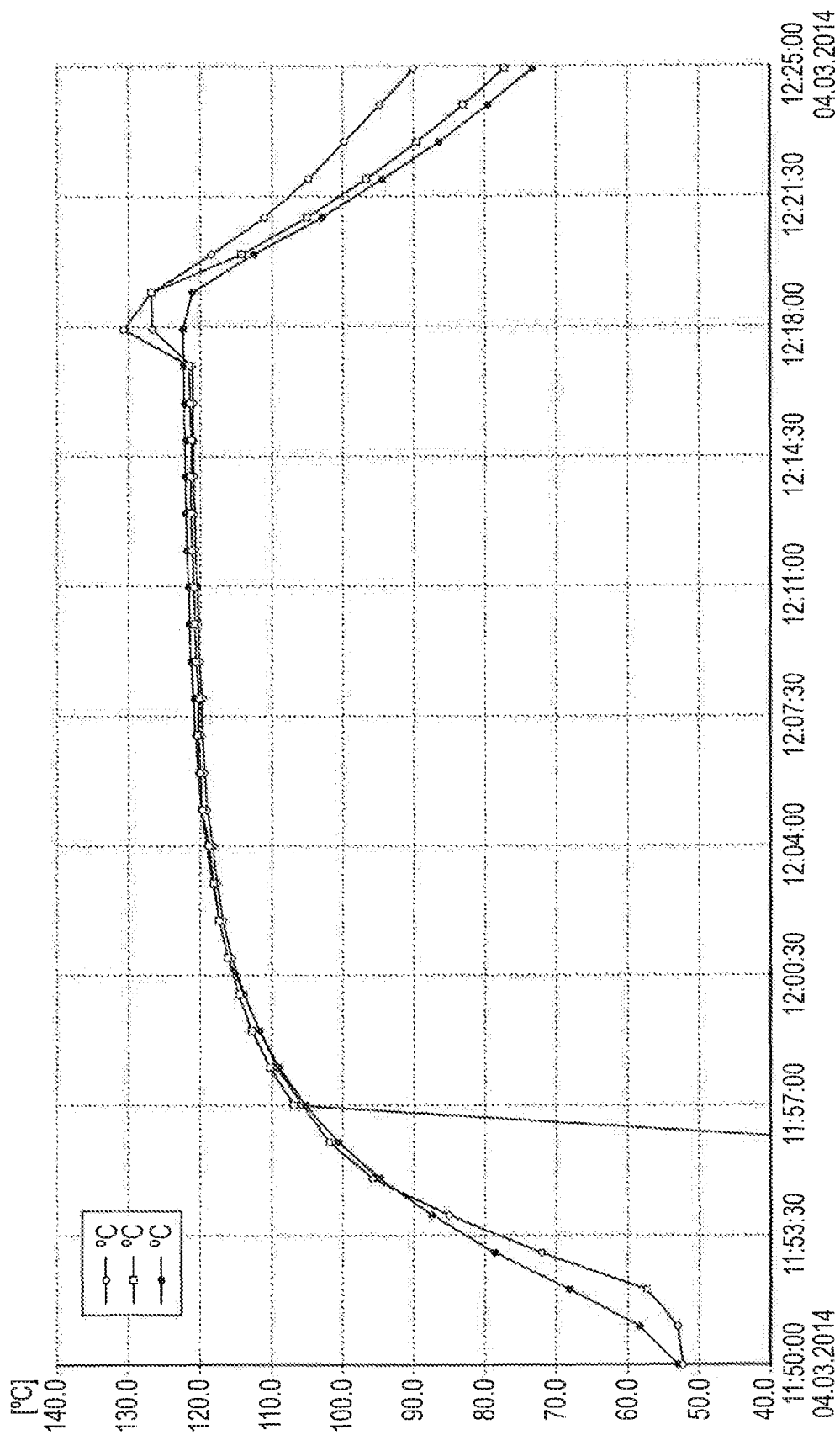
FIG. 3 shows temperature (FIGS. 3a and 3b) and $F_0$ values (FIGS. 3c and 3d) vs. time for an autoclave cycle using initial steam injection/heating jacket with (FIGS. 3b and 3d) and without (FIGS. 3a and 3c) a second steam injection when bulk product has reached $F_0>16$.
Figure 3B:
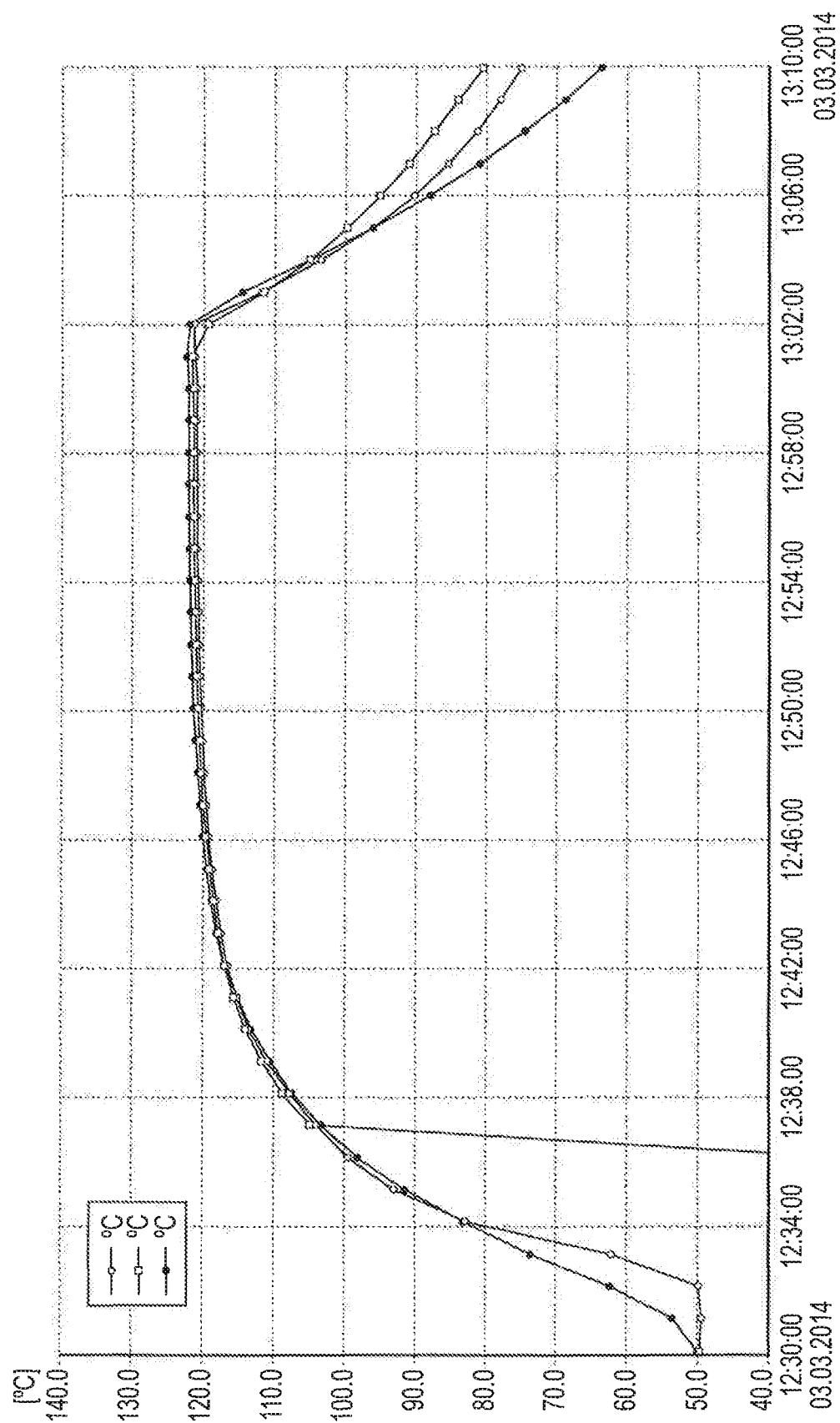
Figure 3C:
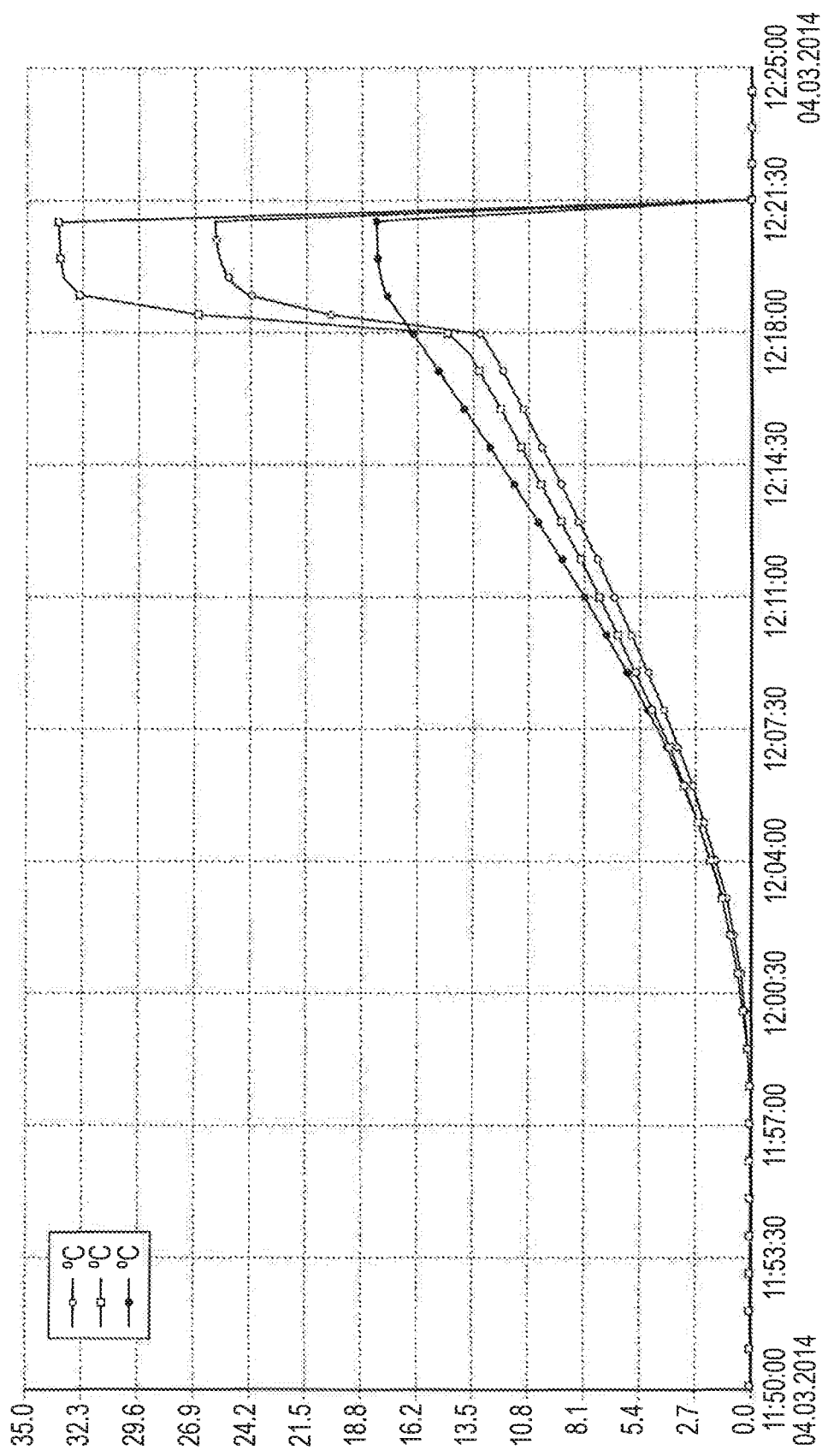
Figure 3D:
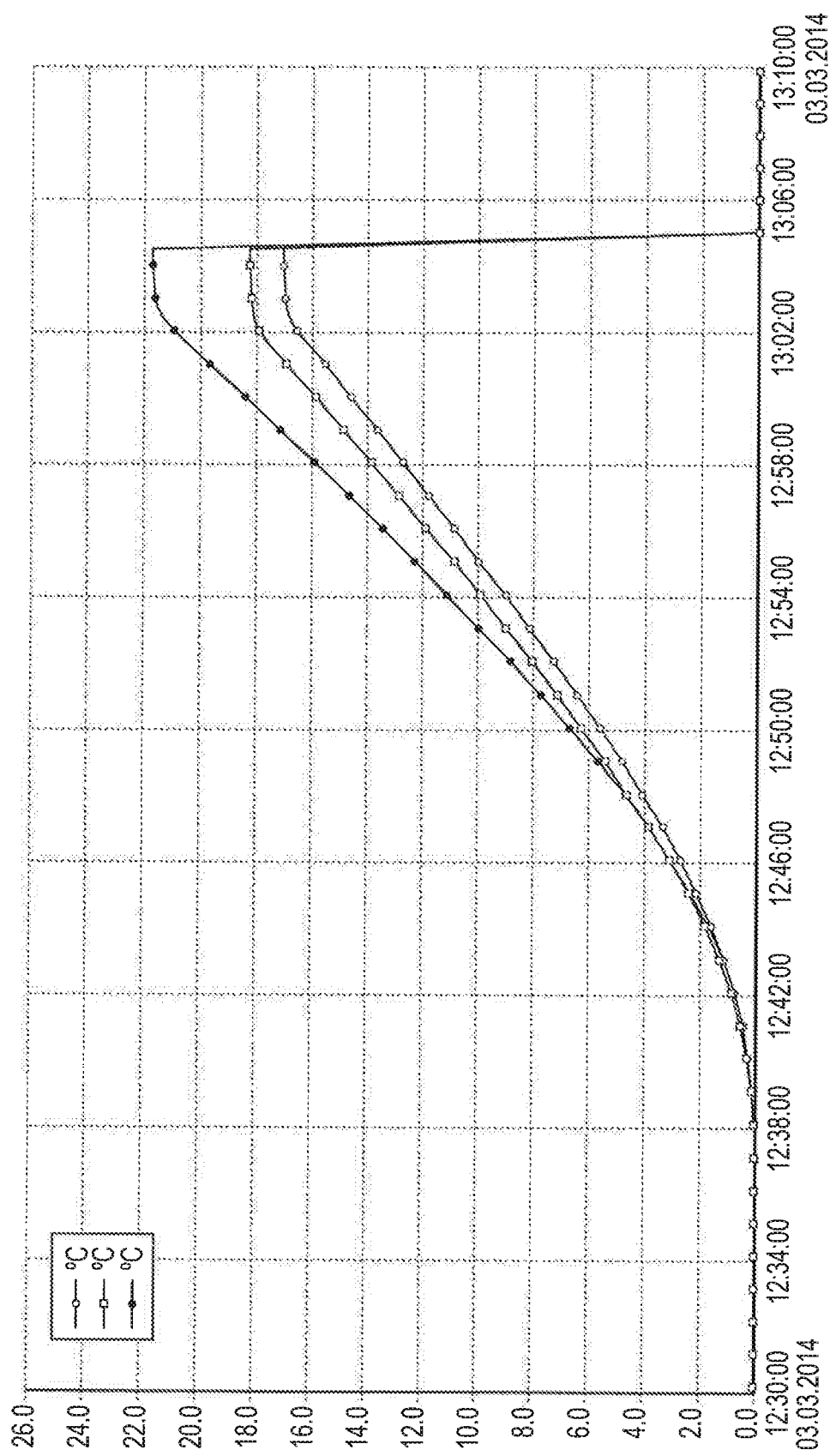

The invention is illustrated by the non-limiting Examples detailed below. Example 1 shows the effectiveness of the steam injection technique of the present invention to achieve a rapid increase in temperature, thus avoiding prolonged heating of the phospholipid suspension (FIG. 2). With the classical methodology, not applying steam injection, the total heat load expressed as time >80° C. before reaching $F_0>16$ is >85 minutes compared to approximately 35 minutes when applying steam injection at the onset of the cycle. Table 1 shows the effect of this difference on the level of PS after autoclaving. When autoclaved with steam injection, the PS content after autoclaving was 83%, decreasing to 75% when autoclaving without steam injection.

Example 2 shows the effectiveness of steam injection at the end of the autoclave cycle (FIGS. 3a-d), where the $F_0$ values of the sterile barriers (inlet port and air filter) almost instantly increases to >16, hence allowing for a further reduction in total heat load (time >80° C.) from approximately 35 minutes to approximately 30 minutes (FIGS. 3a-d). Example 3 provides the preparation of PFB microbubbles stabilised by H-EPS (contrast agent Sonazoid™) using rotor stator mixing.

Example 4 demonstrates the effect of heating time on the autoclave cycle on the lipid composition of the contrast agent Sonazoid™. As can be seen in Table 2, the level of PS decreases on heating, with an associated rise in PA concentration. Table 3 shows that the characteristics of the ultrasound contrast agent deteriorate quite significantly between a 23 ($F_0=25$) and a 30 ($F_0=30$) minute autoclave cycle—such that the latter failed specification on several criteria. This demonstrates the need for careful control of the heating cycle and methodology as per the present invention.

Abbreviations

FD: freeze-drying.
GMP: Good Manufacturing Practice;
H-EPS: hydrogenated egg phosphatidylserine;
ICH: International Conference on Harmonisation;
i.v.: intravenous;
Min: minutes;
PA: phosphatidic acid;
PFB: perfluorobutane;
PS: phosphatidylserine;
Rpm: revolutions per minute;
WFI: water for injection.

EXAMPLE 1: HEATING USING THE HEADSPACE STEAM INJECTION: METHOD I

To study the effect of steam injection on the heat load inflicted on the phospholipids and the ensuing effect on lipid degradation; four autoclave cycles were performed comparing standard cycles with jacket heating only, to cycles where steam was injection to the vessel headspace at the onset of the sterilisation program.

A jacketed, stainless steel pressure vessel (bulk autoclave) from Novaferm (50 L) was utilized. 125 g H-EPS was added to 25 L 10 mg/ml propylene glycol in WFI, and hydrated under stirring at 60° C. for 20 minutes before the autoclave cycle was initiated. A sensor monitored the temperature in the bulk lipid suspension and $F_0$ was calculated continuously. For the steam injection cycles, vacuum was drawn in three cycles from the headspace of the vessel prior to steam injection. Injection of clean steam was performed at the onset of the autoclave cycle. Cooling with water (ambient temperature) was initiated when the $F_0$ value was >16. Using the same H-EPS raw material, two replicate autoclave cycles were repeated both with and without the steam injection procedure.

Results for the temperature in the bulk product vs. time are shown in FIG. 2.

The phospholipid composition of the autoclaved suspension preparations was analysed according to Hvattum et al [J. Pharm. Biomed. Anal., 42, 506-512 (2006)]. The results are summarized in Table 1:

TABLE 1

Content of PS and PA in lipid suspension autoclaved to $F_0 = 16$ using conventional jacket heating with and without injection of steam to vessel headspace. Values given as % of sum of PS and PA.

| Sample | Cycle | PS (%) | PA (%) |
|---|---|---|---|
| 1 | No steam injection | 76.3 | 23.7 |
| 2 | No steam injection | 73.2 | 26.8 |
| 3 | Steam injection | 82.6 | 17.4 |
| 4 | Steam injection | 82.5 | 17.5 |

FIG. 2 and Table 1 shows the effectiveness of the steam injection technique of the present invention to achieve a rapid increase in temperature, thus avoiding prolonged heating of the phospholipid suspension. With the classical methodology, not applying steam injection, the total heat load expressed as time >80° C. before reaching $F_0>16$ is >85 minutes compared to approximately 35 minutes when applying steam injection at the onset of the cycle. In fact, with only conventional heating of the jacket, no sterilisation plateau was established at all.

Table 1 shows the effect of this difference on the levels of PS and PA after autoclaving. Notably, the PS content decreases significantly with increased heat load, whereas the PA content increases. Autoclaved with steam injection the PS content (in % of PS+PA) after autoclaving was 83%, decreasing to 75% when autoclaving without steam injection.

EXAMPLE 2: HEATING USING THE HEADSPACE STEAM INJECTION: METHOD II

To study the effect of steam injection on the heat load inflicted on the phospholipids, autoclave cycles were performed comparing a cycle with jacket heating and steam injection at the onset of the sterilisation program to a cycle where steam was also injected to the headspace when the $F_0$ of the bulk material reached 16.

Figure 1:
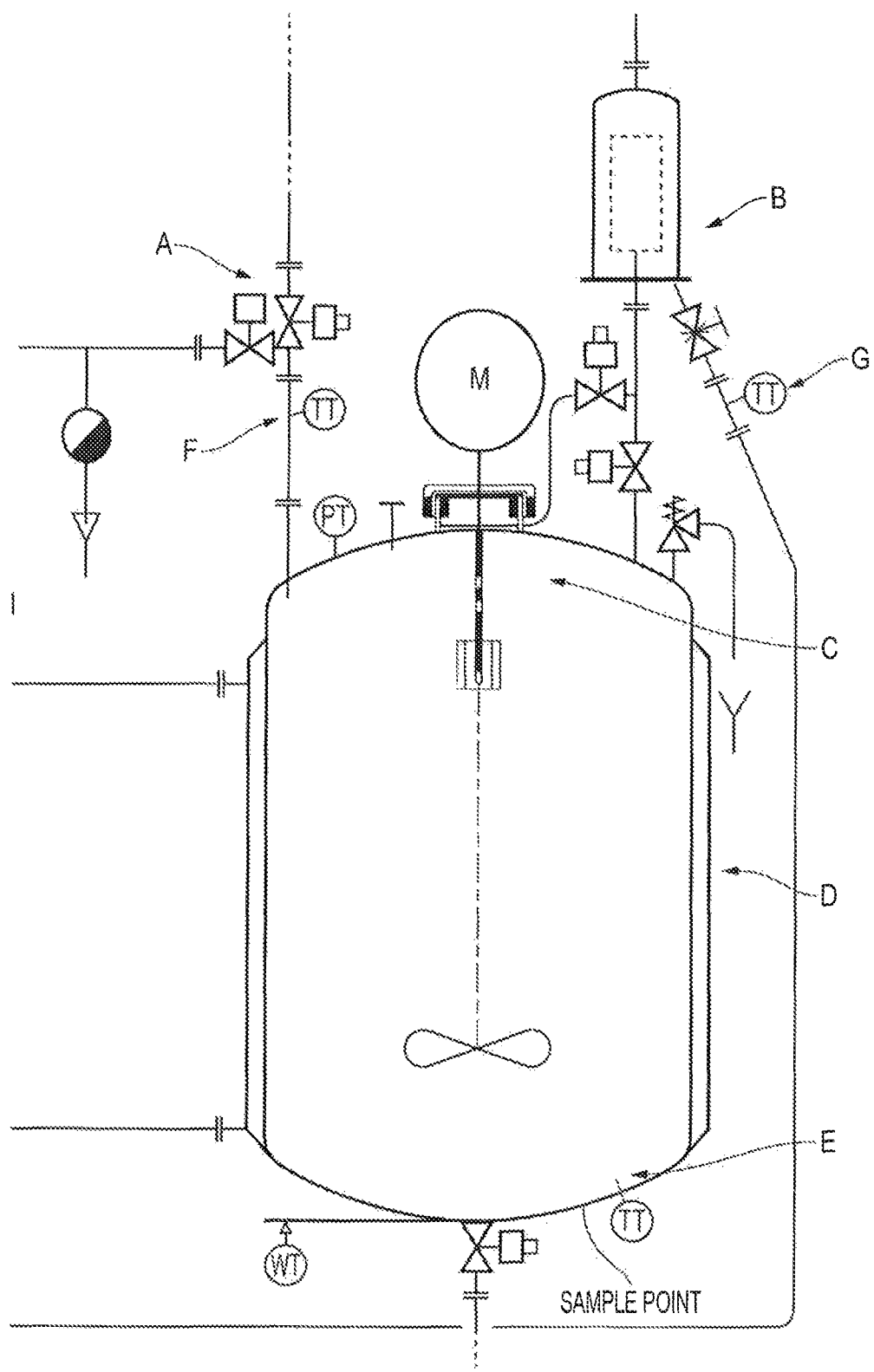
FIG. 1 shows the schematics of a typical system for autoclaving of liquid products such as a lipid suspension; SOL jacketed steel vessel. Points A, B, C, D, E, F and G are medium inlet port, sterile air filter, vessel top, heating jacket, temperature sensor for bulk product, temperature sensor for inlet port and temperature sensor for air filter, respectively.

A jacketed, stainless steel pressure vessel (bulk autoclave) from Diesel (77 L) was utilized. 250 g H-EPS was added to 50 L 10 mg/ml propylene glycol in WFI, and hydrated under stirring at 60° C. for 20 minutes before the autoclave cycle was initiated. Temperature probes were used to monitor the temperature within the phospholipid suspension and at the sterility barriers at the medium inlet and air filter, as noted in FIG. 1. $F_0$ values were continuously calculated for each sensor.

Heating was started by addition of regular house steam (1.25 barG, 124° C.) to the jacket. Three vacuum pulses of 40 s were applied and a 45 s steam injection at 2.35 barG and 137° C. was applied through the medium inlet port. Once the bulk suspension $F_0$ value was >16, the vacuum pulse/steam injection procedure was repeated. Cooling with water (ambient temperature) to the jacket was initiated when the $F_0$ value calculated for both sterility barriers reached >16.

Results for temperature and $F_0$ values at the three sensors vs. time are shown in FIGS. 3a-d.

These results show the effectiveness of steam injection at the end of the autoclave cycle, where the $F_0$ values of the sterile barriers (inlet port and air filter) almost instantly increases to >16, hence allowing for a further reduction in the total heat load inflicted on the phospholipid suspension (expressed as time >80° C.) from approximately 35 minutes to approximately 30 minutes.

EXAMPLE 3: PREPARATION OF SONAZOID™ DRUG PRODUCT BY ROTOR STATOR MIXING AND LYOPHILIZATION

Sterile H-EPS suspensions were prepared as detailed in Example 4. For each batch (A, B and C) Sonazoid™ drug product was manufactures as detailed in the following. A portion (500 mL) of the suspension was transferred to a round-bottomed flask with a conical neck. The flask was fitted with a glass jacket having a temperature control inlet and outlet connected to a water bath maintained at 25° C.

A rotor stator mixing shaft was introduced into the solution and to avoid gas leakage the space between the neck wall and the mixing shaft was sealed with a specially designed metal plug fitted with a gas inlet/outlet connection for adjustment of gas content and pressure control. The gas outlet was connected to a vacuum pump and the solution was degassed for one minute. An atmosphere of perfluoro-n-butane gas was then applied through the gas inlet. The solution was homogenised at 23,000 rpm for 10 min, keeping the rotor stator mixing shaft such that the openings were slightly above the surface of the liquid.

A white-coloured creamy dispersion was obtained, which was transferred to a sealable container and flushed with perfluoro-n-butane. 440 g of the dispersion was then transferred to a flotation/separation tank (85 mm in diameter) for a multistep adjustment of size and concentration. The dispersion was allowed to settle for 400 minutes before 250 mL was drained off through the bottom valve. This procedure was repeated 4 times. An in-process determination of microbubble concentration was then performed by Coulter counting. Based on the result from the in-process analysis, the final dispersion for lyophilisation was then adjusted to a fixed target microbubble concentration of 1.7% v/v. Adjustment of concentration was performed with 184 mg/mL sucrose in WFI and WFI to 92 mg/mL sucrose in the final dispersion. For each batch A, B and C, 2 mL of the final dispersion was transferred to 10 mL sterile glass vials (N=30) with lyophilisation stoppers. Lyophilisation was performed using a Amsco Finn Aqua Lyovac GT6 pilot freeze dryer with a cycle as detailed below.

| Phase | Temperature (° C.) | Time (h) | Pressure (μbar) |
|---|---|---|---|
| Freezing | −60 | 2 | Ambient |
| Primary drying | −32 | 72 | 52 |
| Secondary drying | 34 | 38 | 20 |

EXAMPLE 4: EFFECT OF AUTOCLAVING TIME ON PHOSPHOLIPID CONTENT OF SONAZOID™

To determine the level of degradation in Sonazoid™ product and the effect on critical quality attributes of the level of degradation, sterilisation of the hydrated phospholipid suspension in bulk-autoclave for 15, 23 and 30 minutes was investigated.

A jacketed Buchiglasuster Miniautoclave (1 L) was used. 4 g H-EPS sodium was added to 800 mL of 10 mg/mL propylene glycol in WFI and mixed at 200 rpm at 60° C. for 20 minutes before the autoclave cycle was started. A temperature sensor, placed in the bulk of the suspension was used for continuous monitoring of the suspension temperature. The jacket was supplied from a heated silicon oil bath, kept at 160° C. for the heating period and adjusted to 145° C. when the suspension reached the set temperature of 121° C. The suspension was kept at this temperature for 15, 23 and 30 minutes, for batches A, B and C, respectively (measured temperature varied between 121 and 124° C.). At the end of the cycle, cooling water at 20° C. was applied to the jacket. After reaching room temperature, the sterilized H-EPS suspensions were used for the manufacture of Sonazoid™ as detailed in Example 3.

The Drug Product Sonazoid™ was prepared according to Example 3 in 3 batches A, B and C differing in the autoclaving times (minutes at 121° C.) used for sterilization of the phospholipid suspension. The phospholipid composition of suspensions A, B and C was analysed by TLC according to Hvattum et al [J. Pharm. Biomed. Anal., 42, 506-512 (2006)]. The microbubble concentration and size, the acoustic attenuation efficacy at 3.5 MHz and the pressure stability, as % attenuation efficacy at 3.5 MHz after pressurizing for 60 s at 120 mmHg, was measured as described by Sontum [Ultraso. Med. Biol., 34(5), 824-833 (2008)]. The results are summarized in Tables 2 and 3 below:

These results demonstrate the effect of heating time in the autoclave sterilisation on the lipid composition of the contrast agent Sonazoid™. As can be seen in Table 1, the level of PS decreases on heating, with an associated rise in concentration of PA and other related substances. Table 2 shows that the characteristics of the ultrasound contrast agent deteriorate quite significantly between a 23 ($F_0$=25) and a 30 ($F_0$=30) minute autoclave cycle—such that the latter failed specification on several criteria. This demonstrates the need for careful control of the heating cycle as per the present invention.

As apparent from these data, in order to produce Sonazoid with acceptable characteristics, the amount of PS in percent of total amount of PS and related substances should be at least 68%. The content of PA relative to the total amount of PS and related substances should be less than 15%. Lower PS levels will lead to lowering of yield and inferior microbubble characteristics.

TABLE 2

Lipid composition in Lipid suspension after autoclaving. Identified lipid components and degradation products are detailed in Scheme 1, $I_x$ is sum of unidentified, related degradation products. A data are in mg/mL.

| Sample | PS | PA | FFA | L-PS | L-PA | S | $I_x$ | Sum | PS/Sum |
|---|---|---|---|---|---|---|---|---|---|
| A (15 min) | 3.65 | 0.55 | 0.15 | 0.23 | 0.03 | 0.16 | 0.05 | 4.8 | 0.76 |
| B (23 min) | 3.24 | 0.70 | 0.20 | 0.32 | 0.05 | 0.20 | 0.06 | 4.8 | 0.68 |
| C (30 min) | 3.10 | 0.74 | 0.23 | 0.37 | 0.06 | 0.21 | 0.06 | 4.8 | 0.65 |

TABLE 3

Critical quality attributes of Drug Product

| Parameter | A (15 min) | B (23 min) | C (30 min) |
|---|---|---|---|
| Volume (% v/v) | 0.98% | 0.99% | 0.56%* |
| Median diameter | 2.88 μm | 2.78 μm | 2.4 μm |
| Attenuation at 3.5 MHz | 17.9 dB/cm | 18.8 dB/cm | 9.5 dB/cm* |
| Attenuation after pressure | 92% | 94% | 89.3%* |

*Below specifications.

The invention claimed is:

1. A method of sterilization of a suspension, which comprises:
   (i) mixing a hydrogenated egg phosphatidylserine together with propylene glycol in an aqueous biocompatible carrier using a mixer of a jacketed vessel to give an aqueous hydrogenated egg phosphatidylserine suspension, wherein the suspension contacts an inner wall of the jacketed vessel and the mixer is provided within the jacketed vessel and is configured to mix the contents of the jacketed vessel;
   (ii) autoclaving the aqueous hydrogenated egg phosphatidylserine suspension from step (i), wherein said autoclaving enables reaching $F_0$ values >15 in all parts of the sterilization system, and wherein heating, in addition to sensible heat from heating the jacket of said vessel, comprises the addition of steam to the headspace of the vessel of step (i) to obtain a hot suspension; and
   (iii) cooling the hot suspension to 15 to 30° C. to give the sterile hydrogenated egg phosphatidylserine suspension, wherein the mass ratio of phospholipid to propylene glycol is 1:1.5 to 1:2.5.

2. The method of claim 1, wherein the addition of steam to the headspace is performed multiple times during the autoclave cycle.

3. The method of claim 1, further comprising the application of vacuum to the headspace of the vessel of step (i), before the addition of steam to said headspace.

4. The method of claim 1, wherein the $F_0$ values reacted are between 15 and 25.

5. The method of claim 1, wherein the content of phosphatidylserine (PS), relative to the sum of PS and related substances, in the sterile hydrogenated egg phosphatidylserine suspension of step (iii) is at least 68%.

6. The method of claim 5, wherein the concentration of phosphatidic acid (PA), relative to the sum of PS and related substances, in the sterile p hydrogenated egg phosphatidylserine suspension of step (iii), is less than 15%.

7. The method of claim 6, wherein the combined concentration of phosphatidylserine (PS) and phosphatidic acid (PA) in the sterile hydrogenated egg phosphatidylserine suspension of step (iii) is 5 mg/mL.

8. The method of claim 7, wherein the mass ratio of the hydrogenated egg phosphatidylserine to propylene glycol is 1:2.

9. The method of claim 1, wherein clean steam is used in step (ii).

10. The method of claim 1, wherein a volume of the aqueous hydrogenated egg phosphatidylserine suspension of step (i) is in the range 20 to 80 L.

* * * * *